(12) United States Patent
Connolly et al.

(10) Patent No.: US 8,529,545 B2
(45) Date of Patent: Sep. 10, 2013

(54) ASEPTIC CONNECTOR WITH LIP SEAL

(75) Inventors: Walter L. Connolly, Moraga, CA (US); Mark R. Embury, Fremont, CA (US)

(73) Assignee: ASEPCO, Mountain View, CA (US)

( * ) Notice: Subject to any disclaimer, the term of this patent is extended or adjusted under 35 U.S.C. 154(b) by 1144 days.

(21) Appl. No.: 11/853,249

(22) Filed: Sep. 11, 2007

(65) Prior Publication Data

US 2009/0069791 A1    Mar. 12, 2009

(51) Int. Cl.
*A61M 25/16*    (2006.01)
*A61M 25/18*    (2006.01)
*A61M 39/02*    (2006.01)

(52) U.S. Cl.
USPC ........................................ 604/539

(58) Field of Classification Search
USPC .................... 604/246, 24, 533, 534, 538, 539
See application file for complete search history.

(56) References Cited

U.S. PATENT DOCUMENTS

| | | | |
|---|---|---|---|
| 1,151,131 A * | 8/1915 | Starliper | 403/344 |
| 7,192,003 B2 | 3/2007 | Hoobyar | |
| 2004/0021121 A1* | 2/2004 | Newberg | 251/335.1 |
| 2006/0060812 A1* | 3/2006 | Hoobyar et al. | 251/331 |

* cited by examiner

*Primary Examiner* — Kevin C Sirmons
*Assistant Examiner* — Bradley Osinski
(74) *Attorney, Agent, or Firm* — Edward S. Wright

(57) ABSTRACT

Aseptic connector which has a body, an axially extending opening in the body, a seat surrounding the opening for receiving the connecting flange of a fitting, and a clamp for pressing the flange into the seat. The seat has a radially extending sealing surface with an annular outer portion and a conically inclined inner lip that extends inwardly and upwardly from the annular portion toward the opening.

21 Claims, 4 Drawing Sheets

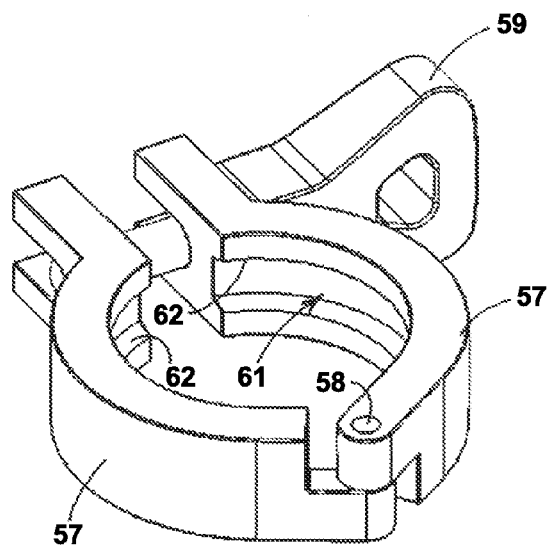

ASEPTIC CONNECTOR WITH LIP SEAL

BACKGROUND OF THE INVENTION

1. Field of Invention

This invention pertains generally to connectors for use in attaching fittings such as valves and pipes to vessels or other sterile containers and, more particularly, to an aseptic connector having a lip seal.

2. Related Art

Valves for use in withdrawing samples of aseptic liquids from mixing vessels and other sterile containers are commonly connected to the containers by a connector having a body which is welded into an opening in a wall of the container and has an annular recess or seat for receiving the mounting flange of the valve, with a ring for clamping the flange in sealing engagement with the bottom wall of the seat. Such connectors have been marketed by a Swedish company, NovaSepticAB, under the trademark NA-CONNECT and by Asepco, Mountain View, Calif., under the trademark ASEP-CONNECT. An example of the use of such a connector is found in Ser. No. 10/947,396.

OBJECTS AND SUMMARY OF THE INVENTION

It is, in general, an object of the invention to provide a new and improved connector for use in attaching fittings such as valves, pipes and sampling systems to mixing vessels or other sterile containers.

Another object of the invention is to provide a connector of the above character which has a lip seal.

These and other objects are achieved in accordance with the invention by providing an aseptic connector which has a body, an axially extending opening in the body, a seat surrounding the opening for receiving the connecting flange of a fitting, and a clamp for pressing the flange into the seat. The seat has a radially extending sealing surface with an annular outer portion and a raised inner lip that is conically inclined and slants inwardly and upwardly from the annular portion toward the opening.

BRIEF DESCRIPTION OF THE DRAWINGS

FIG. 8 is an isometric view of one embodiment of a clamp which can be used in the embodiment of FIG. 5.

DETAILED DESCRIPTION

Figure 1:
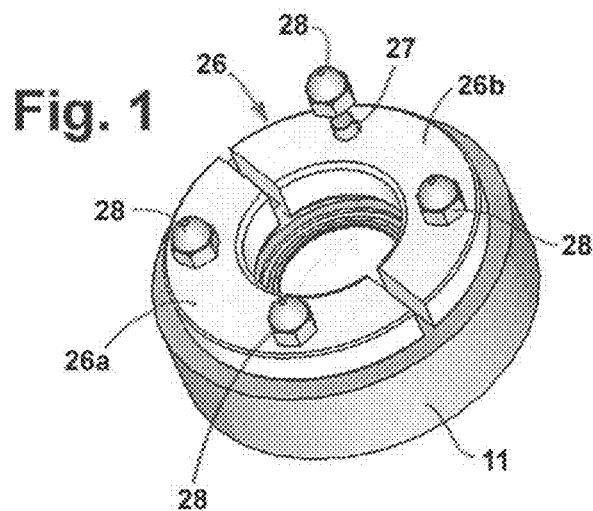
FIG. 1 is an isometric view, partially exploded, of one embodiment of an aseptic connector incorporating the invention.

As illustrated in the drawings, the connector has a cylindrical body 11 with an axially extending central opening or bore 12 and an inlet cone 13 on one side of the body tapering toward the opening. The body is adapted to be welded into a circular opening in the side wall or the bottom wall of a mixing vessel or other sterile container, with the base of the inlet cone facing into the container. In the embodiment illustrated, the body is of substantially greater diameter than length. However, depending upon the size of the fitting with which the connector is to be used, it could have a different diameter-to-length ratio, and the length of the body could even be greater than the diameter.

On the side of the body opposite the inlet cone, a seat 16 is provided for receiving the connecting flange of a fitting such as a valve, a pipe, or a sampling system which is to be connected to the container. The seat is disposed coaxially of opening 12 and inlet cone 13 and has a cylindrical side wall 17 and an annular end wall with a sealing surface 18 which surrounds the opening.

Figure 2:
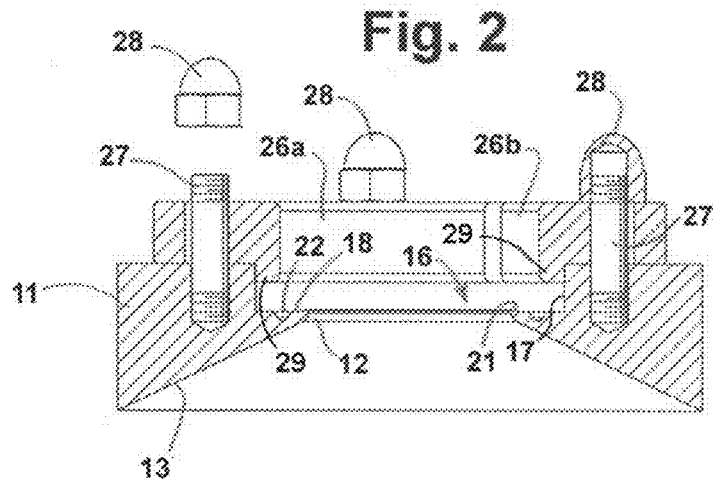
FIG. 2 is a vertical sectional view, partially exploded, of the embodiment of FIG. 1.
Figure 3:
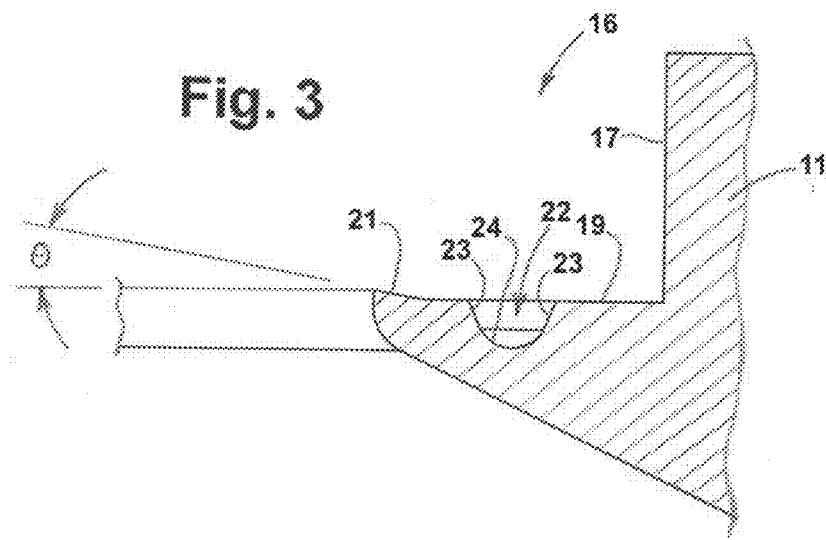
FIG. 3 is an enlarged sectional view of the embodiment of FIG. 1.

The sealing surface has a substantially flat, annular outer portion 19 which lies in a radial plane and an axially extending inner lip portion 21 between the outer portion and the opening. In the embodiment illustrated, the surface of the lip is conically inclined at an angle θ which, in one presently preferred embodiment, is on the order of 10 degrees relative to the plane of the annular outer portion. When the connector is oriented with the seat facing up as shown in FIGS. 2 and 3, the lip is raised relative to the outer annular portion, with the surface of the lip slanting inwardly and upwardly from the inner edge of the annular outer portion toward the opening. Even though the lip will extend in other directions when the connector is oriented differently, it may still be referred to as being "raised" relative to the annular portion, and that will be understood to mean that the lip extends or protrudes from the surface of the annular portion.

An O-ring groove 22 having inclined side walls 23 and a rounded bottom wall 24 is formed in the annular portion of the sealing surface.

A split ring clamp 26 is attached to the body by studs 27 and nuts 28 for pressing the connecting flange of the fitting into the seat 16 and toward sealing surface 18. The studs are threaded into the body near the seat, and the nuts are threaded onto the studs and bear against the surface of the ring. The ring is formed in two sections 26a, 26b, each of which has an inner flange or lip 29 that projects toward the sealing surface for engagement with the flange on the fitting.

The connector is fabricated of a material such as stainless steel which can be thoroughly cleaned and sterilized, and the nuts 28 on the upper portions of the studs 27 are preferably acorn nuts so that the threads are totally enclosed and cannot collect contamination.

Figure 4:
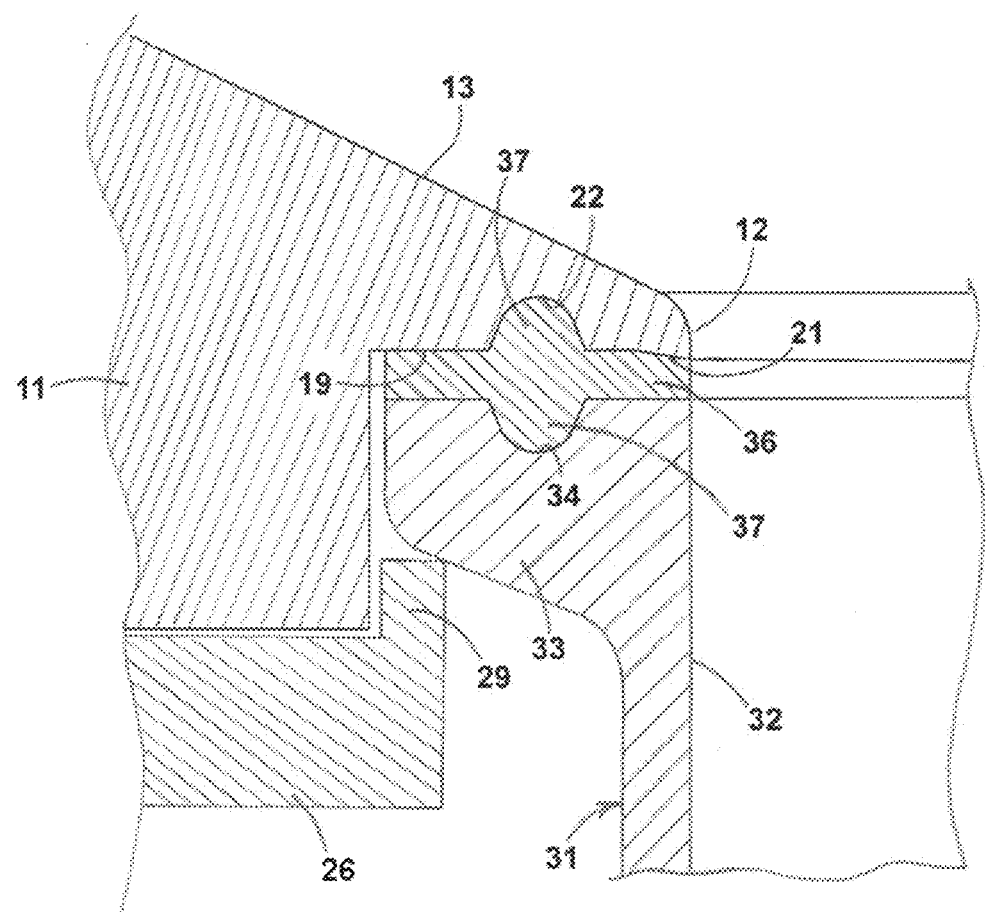
FIG. 4 is a view similar to FIG. 3, but rotated 180 degrees and with a fitting mounted in the connector.

In FIG. 4, the connector is illustrated in connection with a fitting 31 which has an axially extending passageway 32 and a radially extending connecting flange 33 through which the passageway opens. The fitting can, for example, be an aseptic sampling valve of the type shown in Ser. No. 10/947,396. Flange 33 is circular and has an O-ring groove 34 of the same diameter and configuration as O-ring groove 22 in sealing surface 18, and passageway 32 has the same diameter as bore 12. In this figure, the connector is oriented as it would be when welded into an opening in the bottom wall of a container (not shown), with seat 16 facing down and the valve or fitting 31 extending in a downward direction from the container.

An annular gasket 36 is positioned between flange 33 and sealing surface 18. This gasket has beads 37, 37 on opposite faces which are received in the grooves in the flange and the sealing surface, and when nuts 28 are tightened on studs 27, sealing lip 21 is pressed into the gasket to ensure a liquid-tight seal between the fitting and the connector. With the inclined lip, that seal is formed at the inner edge of the seat immediately adjacent to bore 12 and passageway 32, which prevents the product from leaking and becoming entrapped between the seat and the gasket and/or the flange and the gasket.

The lip seal provides a significant improvement and advantage over the prior art. The areas between the gasket and the seat and flange cannot be cleaned without disassembling the system, and without the lip seal, product could collect in those areas and become rancid. Surges in tank pressure could then flush the rancid product back into the product flow, contaminating the product and possibly even making it septic. With the lip seal preventing leakage beyond the walls of the bore in the connector and the passageway in the fitting, the product is confined to areas which are readily cleaned without disassembling the system, and truly aseptic operation is thus made possible.

Figure 5:
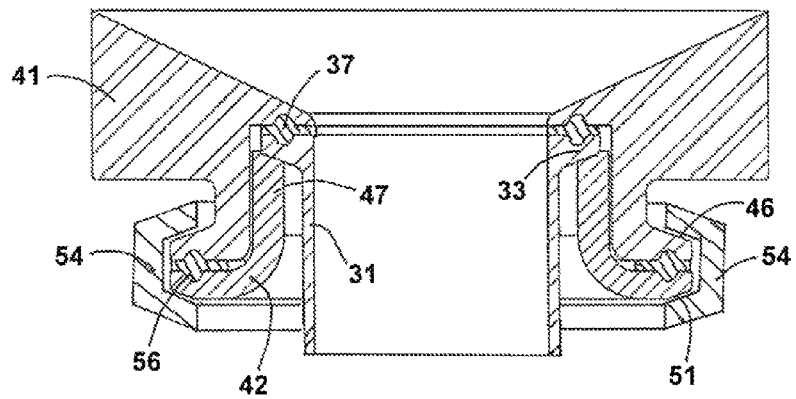
FIG. 5 is a vertical sectional view of another embodiment of an aseptic connector incorporating the invention.
Figure 6:
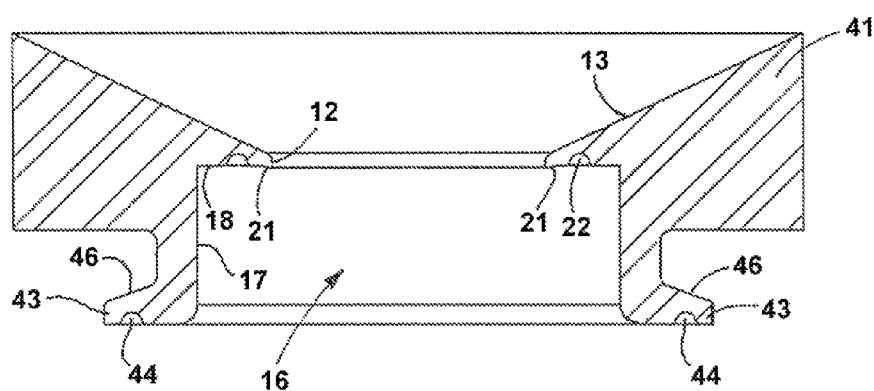
FIG. 6 is a vertical sectional view of the body or base in embodiment of FIG. 5.
Figure 7:
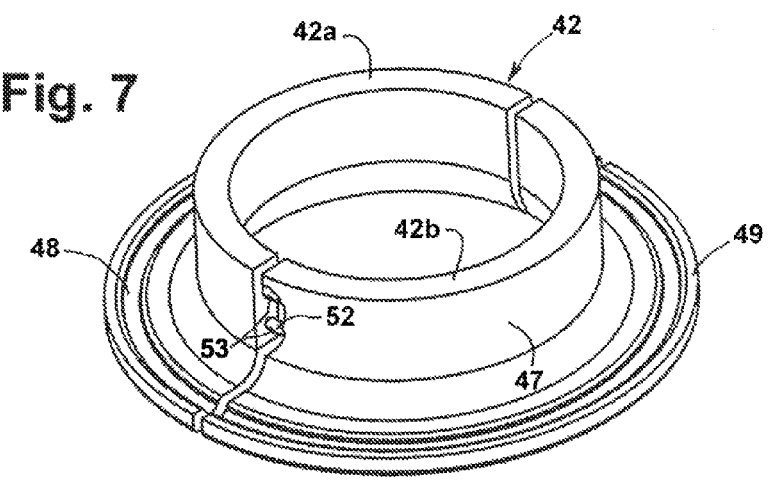
FIG. 7 is an isometric view of the retaining collar in the embodiment of FIG. 5.

The embodiment shown in FIG. 5 includes a body 41 which is generally similar to body 11, and like reference numerals designate corresponding elements in the two embodiments. The embodiment of FIG. 5 also includes a collar 42 which retains a fitting 31 in the seat 16 in the body.

Body 41 has a deeper seat 16 and a longer side wall 17 than body 11, and the outer end of the side wall terminates in a radially extending annular flange 43. Flange 43 has an O-ring groove 44 in its front face and a beveled surface 46 on its back side.

Retaining collar 42 has a cylindrical side wall 47 which terminates in a radially extending annular flange 48 that has an O-ring groove 49 in its rear face and a beveled surface 51 on its front side. Side wall 47 is larger in diameter than the side wall of fitting 31 and smaller in diameter than side wall 17 of seat 16. Thus, as best seen in FIG. 5, collar 42 encircles the side wall of the fitting, with the inner end of side wall 47 bearing against the rear surface of flange 33 on fitting 31.

Collar 42 is split diametrically into two sections 42a, 42b, with locating pins 52 extending between the two sections for holding the sections in proper alignment in the seat. The pins can be fixedly mounted to one section and removably received in aligned bores 53 in the other to permit the two sections to be separated and then brought together around the fitting and inserted into the seat. Alternately, the pins can be removably received in aligned bores in both sections.

A clamp 54 of the type commonly known as a tri clamp encircles the flanges and engages the beveled surfaces 46, 51 on opposite sides of the flanges to urge the flanges together and press the collar into the seat, with the inner end of side wall 47 bearing against flange 33 to press it toward sealing surface 18. In this embodiment, a second seal is provided between flanges 43, 48 by an annular beaded gasket 56.

A suitable tri clamp for use in the embodiment of FIG. 5 is shown in FIG. 8. This clamp has a pair of semi-circular jaws 57, 57 which are connected together on one side by a pivot pin 58, with a screw 59 on the opposite side for drawing the two jaws together. A groove 61 opens through the inner side walls of the jaws and has sloping walls 62, 62 which engage the beveled surfaces 46, 51 of the flanges as the clamp is tightened about the flanges.

The invention has a number of important features and advantages, with the tapered lip on the sealing surface providing a definitive seal at the bore which makes aseptic operation possible even in the presence of pressure surges. It is apparent from the foregoing that a new and improved aseptic connector has been provided. While only certain presently preferred embodiments have been described in detail, as will be apparent to those familiar with the art, certain changes and modifications can be made without departing from the scope of the invention as defined by the following claims.

The invention claimed is:

1. An aseptic connector for use with a fitting having a radially extending connecting flange and an axially extending passageway which opens through the flange, comprising a body, an axially extending opening in the body, a seat surrounding the opening for receiving the flange with the passageway in the fitting communicating with the opening in the body, the seat having a radially extending sealing surface with a substantially flat outer portion disposed in a radial plane and a conically inclined inner lip extending from the outer portion to the opening, and a clamp for pressing the flange into the seat toward the sealing surface.

2. The aseptic connector of claim 1 wherein the opening in the body and the passageway in the fitting have side walls of like configuration, and a seal is formed between the lip and the flange at the side walls of the opening and the passageway.

3. The aseptic connector of claim 1 including a gasket between the flange and the sealing surface.

4. The aseptic connector of claim 1 wherein the sealing lip is inclined at an angle on the order of 10 degrees relative to the plane of the substantially flat outer portion of the sealing surface.

5. The aseptic connector of claim 1 including an O-ring groove in the substantially flat outer portion of the sealing surface.

6. The aseptic connector of claim 1 wherein the clamp includes a split ring engagable with the connecting flange and threaded fasteners engaging the split ring for drawing the flange toward the seat.

7. The aseptic connector of claim 1 including a collar which encircles the fitting and has a side wall which bears against the connecting flange, with the body and the collar also having clamping flanges and the clamp engaging the clamping flanges of the body and the collar to draw the collar and, hence, the connecting flange of the fitting into the seat toward the sealing surface.

8. An aseptic connector comprising a rigid cylindrical body, an opening passing axially through the body, a seat surrounding the opening and having a radially extending sealing surface with an annular outer portion and a raised sealing lip immediately adjacent to the opening.

9. The aseptic connector of claim 8 wherein the sealing lip has a conically inclined surface which extends to the opening, with the lip being of maximum height at the opening.

10. The aseptic connector of claim 8 wherein the sealing lip has a conically inclined surface which is inclined at an angle on the order of 10 degrees relative to the plane of the annular portion of the sealing surface.

11. The aseptic connector of claim 8 including an O-ring groove in the annular portion of the sealing surface.

12. An aseptic connector for use with a fitting having a radially extending connecting flange, comprising a rigid cylindrical body, an opening passing axially through the body, a seat surrounding the opening having a radially extending sealing surface with a substantially flat outer portion disposed in a radial plane and a raised lip immediately adjacent to the opening, a split ring spaced from the sealing surface for engagement with the flange, and threaded fasteners engaging the body and the split ring for drawing the flange toward the sealing surface.

13. The aseptic connector of claim 12 wherein the raised lip has a conically inclined surface which is inclined at an angle on the order of 10 degrees relative to the plane of the annular portion of the sealing surface.

14. The aseptic connector of claim 12 including a gasket between the flange and the sealing surface.

15. The aseptic connector of claim 12 wherein the threaded fasteners include studs threaded into the body and nuts threadedly mounted on the studs.

16. An aseptic connector for use with a fitting having a radially extending connecting flange, comprising a rigid cylindrical body, an opening passing axially through the body, a seat surrounding the opening having a radially extending sealing surface with a substantially flat outer portion disposed in a radial plane and a raised lip immediately adjacent to the opening, a collar which encircles the fitting and has a side wall that bears against the connecting flange, radially extending clamping flanges on the body and the collar, and a clamp which engages the clamping flanges and draws the collar and, hence, the connecting flange of the fitting into the seat toward the sealing surface.

17. The aseptic connector of claim 16 wherein the raised lip has a conically inclined surface which is inclined at an angle on the order of 10 degrees relative to the plane of the annular portion of the sealing surface.

18. The aseptic connector of claim 16 wherein the collar is split diametrically into two sections, with locating pins extending between the two sections to hold the sections in alignment.

19. The aseptic connector of claim 16 wherein the clamping flanges are annular flanges which extend radially from the body and the side wall of the collar in axial alignment with each other.

20. The aseptic connector of claim 19 wherein the clamping flanges have beveled surfaces on opposite sides thereof, and the clamp encircles the flanges and engages the beveled surfaces for drawing the flanges together when tightened peripherally about the flanges.

21. The aseptic connector of claim 19 including a first gasket between the connecting flange and the sealing surface and a second gasket between the clamping flanges.

* * * * *